(12) United States Patent
Fojtik

(10) Patent No.: US 8,672,900 B2
(45) Date of Patent: *Mar. 18, 2014

(54) HAND-HELD, HAND-OPERATED POWER SYRINGE AND METHODS

(75) Inventor: Shawn P. Fojtik, Park City, UT (US)

(73) Assignee: Mallinckrodt LLC, Hazelwood, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/102,028

(22) Filed: May 5, 2011

(65) Prior Publication Data

US 2011/0213245 A1 Sep. 1, 2011

Related U.S. Application Data

(63) Continuation of application No. 11/431,377, filed on May 9, 2006, now Pat. No. 7,988,677, which is a continuation-in-part of application No. 09/864,967, filed on May 24, 2001, now Pat. No. 7,041,084.

(51) Int. Cl.
*A61M 5/315* (2006.01)

(52) U.S. Cl.
USPC .................. 604/218; 604/223; 604/228

(58) Field of Classification Search
USPC ......... 604/181, 187, 218, 223, 224, 227, 228, 604/232, 233, 234, 235, 246; 222/465.1, 222/469, 470, 471, 472, 473, 474
See application file for complete search history.

(56) References Cited

U.S. PATENT DOCUMENTS

| | | |
|---|---|---|
| 530,187 A | 12/1894 | Laskey |
| 870,573 A | 11/1907 | Myers |
| 901,567 A | 10/1908 | Utschig |
| 1,019,207 A | 3/1912 | Ward |
| 1,218,513 A | 3/1917 | Biron |
| 1,718,596 A | 6/1929 | Smith |
| 3,016,897 A | 1/1962 | Kendrick |
| 3,110,310 A | 11/1963 | Cislak |
| 3,770,169 A | 11/1973 | Roach |
| 4,020,838 A | 5/1977 | Phillips et al. |
| 4,067,334 A | 1/1978 | Haller |
| 4,204,539 A | 5/1980 | Van Brugge |
| 4,330,070 A | 5/1982 | Doubleday |
| 4,364,388 A | 12/1982 | Cech |
| 4,425,121 A | 1/1984 | Young et al. |
| 4,574,803 A | 3/1986 | Storz |
| 4,581,021 A | 4/1986 | Landau et al. |

(Continued)

FOREIGN PATENT DOCUMENTS

| | | |
|---|---|---|
| DE | 7705342 | 6/1977 |
| EP | 0474218 | 3/1992 |

(Continued)

*Primary Examiner* — Theodore Stigell

(57) ABSTRACT

A hand-held syringe includes a handle configured for suspending and using the syringe with a single hand. The handle includes pivotally connected first and second members. The members of the handle may be pivotally connected at intermediate positions along the lengths thereof or at or near ends thereof. The first member is associated with, and may be pivotally connected to, a syringe barrel, while the second member is associated with, and may be pivotally connected to, a syringe plunger. The syringe may be configured for a single-use (i.e., it may be disposable). Applications of use and methods of using a hand-held syringe are also disclosed.

13 Claims, 7 Drawing Sheets

(56) References Cited

U.S. PATENT DOCUMENTS

| | | | |
|---|---|---|---|
| 4,632,669 | A | 12/1986 | Phipps, Sr. et al. |
| 4,657,533 | A | 4/1987 | Oscarsson |
| 4,712,545 | A | 12/1987 | Honkanen |
| 4,715,378 | A | 12/1987 | Pope, Jr. et al. |
| 4,737,151 | A | 4/1988 | Clement et al. |
| 4,738,664 | A | 4/1988 | Prindle |
| 4,744,789 | A | 5/1988 | Johnson |
| 4,799,921 | A | 1/1989 | Johnson et al. |
| 4,808,165 | A | 2/1989 | Carr |
| 4,832,692 | A | 5/1989 | Box et al. |
| 4,861,339 | A | 8/1989 | Jonischkeit |
| 4,968,303 | A | 11/1990 | Clarke et al. |
| 4,994,065 | A | 2/1991 | Gibbs et al. |
| 5,027,605 | A | 7/1991 | Hardesty |
| 5,037,399 | A | 8/1991 | Reichert et al. |
| 5,069,421 | A | 12/1991 | Kishi et al. |
| 5,078,690 | A * | 1/1992 | Ryan .................... 604/187 |
| 5,112,307 | A | 5/1992 | Haber et al. |
| 5,133,483 | A | 7/1992 | Buckles |
| 5,135,507 | A | 8/1992 | Haber et al. |
| 5,139,488 | A | 8/1992 | Klein |
| 5,150,488 | A | 9/1992 | Yuan et al. |
| 5,176,647 | A | 1/1993 | Knoepfler |
| 5,188,610 | A | 2/1993 | Rains |
| 5,228,883 | A | 7/1993 | Blakely et al. |
| 5,282,800 | A | 2/1994 | Foshee et al. |
| 5,288,285 | A | 2/1994 | Carter |
| 5,304,147 | A | 4/1994 | Johnson et al. |
| 5,306,147 | A | 4/1994 | Dragan et al. |
| 5,308,358 | A | 5/1994 | Bond et al. |
| 5,330,074 | A | 7/1994 | Wirsig et al. |
| 5,332,122 | A | 7/1994 | Herold et al. |
| 5,335,586 | A | 8/1994 | Casto et al. |
| 5,336,201 | A | 8/1994 | von der Decken |
| 5,350,365 | A | 9/1994 | De Godoy Moreira |
| 5,350,391 | A | 9/1994 | Iacovelli |
| 5,352,235 | A | 10/1994 | Koros et al. |
| 5,368,202 | A | 11/1994 | Smrt |
| 5,425,743 | A | 6/1995 | Nicholas |
| 5,439,131 | A | 8/1995 | Kato |
| 5,472,451 | A | 12/1995 | Freitas et al. |
| 5,480,409 | A | 1/1996 | Riza |
| 5,499,998 | A | 3/1996 | Meade |
| 5,507,727 | A | 4/1996 | Crainich |
| 5,507,730 | A | 4/1996 | Haber et al. |
| 5,511,556 | A | 4/1996 | DeSantis |
| 5,514,071 | A | 5/1996 | Sielaff, Jr. et al. |
| 5,531,708 | A | 7/1996 | Woodruff |
| 5,560,373 | A | 10/1996 | De Santis |
| 5,562,655 | A | 10/1996 | Mittelstadt et al. |
| 5,569,208 | A | 10/1996 | Woelpper et al. |
| 5,591,135 | A | 1/1997 | Sullivan |
| 5,591,176 | A | 1/1997 | Henderson et al. |
| 5,645,561 | A | 7/1997 | Smith et al. |
| 5,722,829 | A | 3/1998 | Wilcox et al. |
| 5,733,258 | A | 3/1998 | Lane |
| 5,735,874 | A | 4/1998 | Measamer et al. |
| 5,749,968 | A | 5/1998 | Melanson et al. |
| 5,755,362 | A | 5/1998 | Rodriguez, Jr. et al. |
| 5,807,340 | A | 9/1998 | Pokras |
| 5,830,194 | A | 11/1998 | Anwar et al. |
| 5,851,214 | A | 12/1998 | Larsen et al. |
| 5,881,928 | A | 3/1999 | Register et al. |
| 5,893,488 | A | 4/1999 | Hoag et al. |
| 5,951,517 | A | 9/1999 | Lampropoulos et al. |
| 5,961,494 | A | 10/1999 | Hogan |
| 5,961,496 | A | 10/1999 | Nielsen et al. |
| 5,964,380 | A | 10/1999 | Hazzard et al. |
| 5,964,736 | A | 10/1999 | Lane |
| 5,968,017 | A | 10/1999 | Lampropoulos et al. |
| 5,992,694 | A | 11/1999 | Keller |
| 6,004,295 | A | 12/1999 | Langer et al. |
| 6,007,515 | A | 12/1999 | Epstein et al. |
| 6,024,728 | A | 2/2000 | Schulz |
| 6,030,368 | A | 2/2000 | Anwar et al. |
| 6,047,861 | A | 4/2000 | Vidal et al. |
| 6,059,759 | A | 5/2000 | Mottola et al. |
| 6,080,136 | A | 6/2000 | Trull et al. |
| 6,117,158 | A | 9/2000 | Measamer et al. |
| 6,139,563 | A | 10/2000 | Cosgrove, III et al. |
| 6,183,444 | B1 | 2/2001 | Glines et al. |
| 6,213,984 | B1 * | 4/2001 | Lane et al. .................... 604/207 |
| 6,241,708 | B1 | 6/2001 | Reilly et al. |
| 6,264,637 | B1 | 7/2001 | Hogan |
| 6,368,307 | B1 | 4/2002 | Ziemba et al. |
| 6,406,460 | B1 | 6/2002 | Hogan |
| 6,439,439 | B1 | 8/2002 | Rickard et al. |
| 6,585,696 | B2 | 7/2003 | Petersen et al. |
| 6,607,512 | B2 | 8/2003 | Oliver et al. |
| 6,752,781 | B2 | 6/2004 | Landau et al. |
| 6,764,466 | B1 | 7/2004 | Staats et al. |
| 6,802,824 | B2 | 10/2004 | Mickley et al. |
| 7,041,084 | B2 | 5/2006 | Fojtik |
| 7,097,636 | B2 | 8/2006 | Pessin |
| 7,125,395 | B2 | 10/2006 | Hommann et al. |
| 7,240,882 | B2 | 7/2007 | Degentesh et al. |
| 7,534,234 | B2 | 5/2009 | Fojtik |
| 7,988,677 | B2 * | 8/2011 | Fojtik .................... 604/223 |
| 2002/0022805 | A1 | 2/2002 | Lane |
| 2002/0183698 | A1 | 12/2002 | Quinn et al. |
| 2004/0116873 | A1 | 6/2004 | Fojtik |
| 2004/0116893 | A1 | 6/2004 | Spohn et al. |
| 2004/0210200 | A1 | 10/2004 | Gerondale et al. |
| 2005/0070848 | A1 | 3/2005 | Kim et al. |
| 2005/0137575 | A1 | 6/2005 | Thompson et al. |
| 2006/0247578 | A1 | 11/2006 | Arguedas et al. |
| 2007/0010788 | A1 | 1/2007 | Evans |
| 2007/0265573 | A1 | 11/2007 | Fojtik |
| 2010/0249719 | A1 * | 9/2010 | Fojtik .................... 604/218 |

FOREIGN PATENT DOCUMENTS

| | | |
|---|---|---|
| EP | 0565045 | 10/1993 |
| EP | 0577354 | 1/1994 |
| EP | 1066797 | 1/2001 |
| EP | 0919251 | 1/2007 |
| EP | 1148834 | 4/2007 |
| EP | 1301227 | 11/2007 |
| FR | 2668060 | 4/1992 |
| GB | 27811 | 0/1909 |
| GB | 2022421 | 12/1979 |
| JP | 11133030 | 5/1999 |
| WO | 9908735 | 2/1999 |
| WO | 02094343 | 11/2002 |
| WO | 2004062713 | 7/2004 |

* cited by examiner

HAND-HELD, HAND-OPERATED POWER SYRINGE AND METHODS

CROSS-REFERENCE TO RELATED APPLICATION

This application is a continuation of application Ser. No. 11/431,377, filed May 9, 2006, now U.S. Pat. No. 7,988,677, issued on Aug. 2, 2011, which is a continuation-in-part of application Ser. No. 09/864,967, filed May 24, 2001, now U.S. Pat. No. 7,041,084, issued May 9, 2006. Priority is claimed to each of these applications.

BACKGROUND OF THE INVENTION

1. Field of the Invention

The present invention relates generally to apparatus for facilitating the movement of a plunger of a syringe through a barrel of the syringe and, more particularly, to hand-held, hand operated apparatus that facilitate the movement of a plunger through a syringe barrel. More specifically, the present invention relates to hand-held apparatus with scissor grip type leveraged triggering systems that force a plunger of a syringe through the length of the barrel of the syringe.

2. Background of Related Art

Apparatus that facilitate the ejection of fluids from syringes are well known. Such apparatus are often referred to as "fluid delivery devices" or "power syringes."

Conventionally, fluid delivery devices have been used to inject liquids, such as contrasting media (e.g., dyes, carbon dioxide, etc.) and medicines into patients. With many fluid delivery devices, the rate at which a fluid is injected into a patient's body may be controlled. While some of these devices are automated, others may be manually operated.

Due to the increase in delivery force provided by fluid delivery devices, such devices are particularly useful for injecting high viscosity fluids, which would otherwise be difficult, if not impossible, to inject by forcing one's thumb against the plunger of a conventional hand-held syringe.

Some hand-held power syringes, such as that disclosed in U.S. Pat. No. 5,330,074, issued to Wirsig et al. (hereinafter "the '074 Patent"), include ratcheting type mechanisms to assist a user in applying force to a plunger of the syringe. Ratcheting mechanisms are, however, often complex and, consequently, add to the manufacturing costs of such hand-held power syringes.

Other hand-held fluid delivery devices include handles with a fixed member and a movable member associated therewith. In one example of such a syringe, disclosed in U.S. Pat. No. 6,059,759, issued to Lampropoulos et al. (hereinafter "the '759 Patent"), the movable member may be slidingly secured to the fixed member. A plunger is forced into a syringe barrel as a user squeezes the handle members toward one another. Nonetheless, such a syringe only assists the user in forcing the plunger into the syringe barrel by transferring the location where force must be applied and increasing the area of a member to which force must be applied. Alternatively, the ends of the movable member and the fixed member of the handle may be pivotally secured to one another, as described in U.S. Pat. No. 6,024,728, issued to Schulz (hereinafter "the '728 Patent"). In either event, an upper end of the movable member either directly or indirectly engages a plunger of the syringe. Upon squeezing the two members of the handle, the movable member moves toward the fixed member and forces the plunger into the barrel of the syringe. Thus, the handle of such a syringe allows the force provided by a hand squeeze to be applied to the plunger of the syringe rather than the lesser amount of force that would otherwise be provided by use of a thumb to force the plunger into the syringe. Nonetheless, these fluid delivery devices may be difficult to use when the injection of high viscosity fluids is required, which may cause physical or mental discomfort to a patient into whom the fluid is being injected.

Some fluid delivery devices provide leverage to assist a user in forcing a plunger into or out of a syringe barrel. Examples of such devices are provided in U.S. Pat. No. 6,030,368, issued to Anwar et al. (hereinafter "the '368 Patent") and U.S. Pat. No. 4,737,151, issued to Clement et al. (hereinafter "the '151 Patent"). The devices of the '368 and '151 Patents each include three pivot points to provide the desired amount of leverage: a first pivot point connecting a handle member to a plunger; a second pivot point connecting the handle member to a base member; and a third pivot point connecting the base member to a syringe barrel. While the base members of these devices are configured to be supported upon a table top or other flat surface, the generally straight handle members of these devices are configured to receive a downward force by a user, which is transferred to the plunger. As a user need only grip and move the handle member of such a device to move the plunger, the user can apply more force to the handle than that provided by a squeeze of the hand. Nonetheless, due to the manner in which the increased amount of force is applied, it is difficult for a user to make fine adjustments when injecting fluid into a body or extracting fluid therefrom.

Accordingly, there is a need for a fluid delivery apparatus that converts a small amount of controllable force, such as that provided by a squeeze of a hand, to a syringe plunger to facilitate movement of the plunger through a syringe barrel.

SUMMARY OF THE INVENTION

A fluid delivery apparatus incorporating teachings of the present invention is a hand-held type power syringe which includes a handle that is leveraged in such a manner as to apply an increased amount of pressure to the plunger of the syringe. The fluid delivery apparatus of the present invention may also include a syringe barrel with a fluid receptacle formed therethrough, as well as a plunger that inserts into a large end of the receptacle and that may be moved through at least a portion of the length of the receptacle. Fluid delivery apparatus according to the present invention may be configured such that the barrel and plunger of a syringe move simultaneously.

In one aspect, the present invention includes fluid delivery apparatus with a handle that includes pivotally connected members, one of which is secured in relation to a barrel of a syringe, the other of which is secured in relation to a plunger of the syringe. The members of the handle are configured and oriented relative to one another in such a way as to facilitate manipulation and use of the fluid delivery apparatus with one hand. A first member may be rigidly, flexibly, or pivotally associated with the syringe barrel, while the second member may be rigidly, flexibly, or pivotally associated with the syringe plunger.

In an example of an embodiment of a handle that includes three pivot points, the handle may resemble a scissors and includes two members, a first of which is configured to be held by the fingers of an individual and the second of which is configured to be held by the individual's thumb or positioned against the palm of the individual. The members of the handle are oriented so as to cross one another at the pivot point therebetween. One or both of the first and second handle members may enable the user to grip both members with one hand while having a configuration (e.g., a shape, bend, etc.)

that provides a user with a mechanical advantage while maximizing the amount of leverage provided as the handle members are forced toward one another. The two members of the handle are pivotally connected at intermediate, or somewhat central, locations along the lengths thereof. When the first and second members of the handle are moved toward or away from one another, the first pivot point may remain in a substantially fixed position along the lengths of both the first and second members. Alternatively, the first pivot point may move in an elongate path relative to one or both of the first and second members of the handle as the positions of the first and second members are changed relative to one another. By way of example only, the first pivot point may move either eccentrically or in a linear fashion relative to one of the handle members as the positions of the members change while remaining substantially stationary relative to the other handle member.

In another embodiment, in which handles are also arranged to facilitate holding and use of the fluid delivery apparatus with a single hand, the handles may be pivotally connected to one another at or near the ends thereof. A forward (finger) handle is associated with a barrel of a syringe, which may be secured to that handle or allowed to slide therethrough, while a rearward (thumb) handle captures the end of a plunger of the syringe. One or both of these relationships, or "connection points," between the handles and the members of a plunger may include a pivot or include sufficient tolerance to accommodate arcuate movement of the connection points relative to one another as the handles are moved together or apart from each other.

In both reusable and single-use variations of a fluid delivery apparatus of the present invention, the aforementioned elements may be part of a single, integral syringe, or the handles may be configured for association with a separate, disposable syringe.

As an example of the use of a fluid delivery apparatus incorporating teachings of the present invention, a fluid to be injected into a patient may be drawn into the receptacle of the syringe barrel by moving the first and second members away from one another. Air may then be removed from a catheter or needle (e.g., a hypodermic needle or biopsy needle) that communicates with an end of the receptacle by squeezing the first and second members of the handle toward one another and the consequent movement of the plunger partially into the receptacle of the syringe barrel. If a catheter is coupled to the syringe, the catheter may be introduced into the patient or coupled with a catheter that has already been introduced into the patient. The fluid may then be injected into the patient through the needle or one or more catheters by further squeezing of the first and second handle members, which results in the plunger being moved further into the receptacle of the syringe barrel and displacement of fluid located in the receptacle and the catheter.

Other features and advantages of the present invention will become apparent to those of ordinary skill in the art through consideration of the ensuing description, the accompanying drawings, and the appended claims.

BRIEF DESCRIPTION OF THE DRAWINGS

In the drawings, which illustrate exemplary embodiments of fluid delivery apparatus incorporating teachings of the present invention and features thereof.

DETAILED DESCRIPTION OF THE INVENTION

Figure 1:
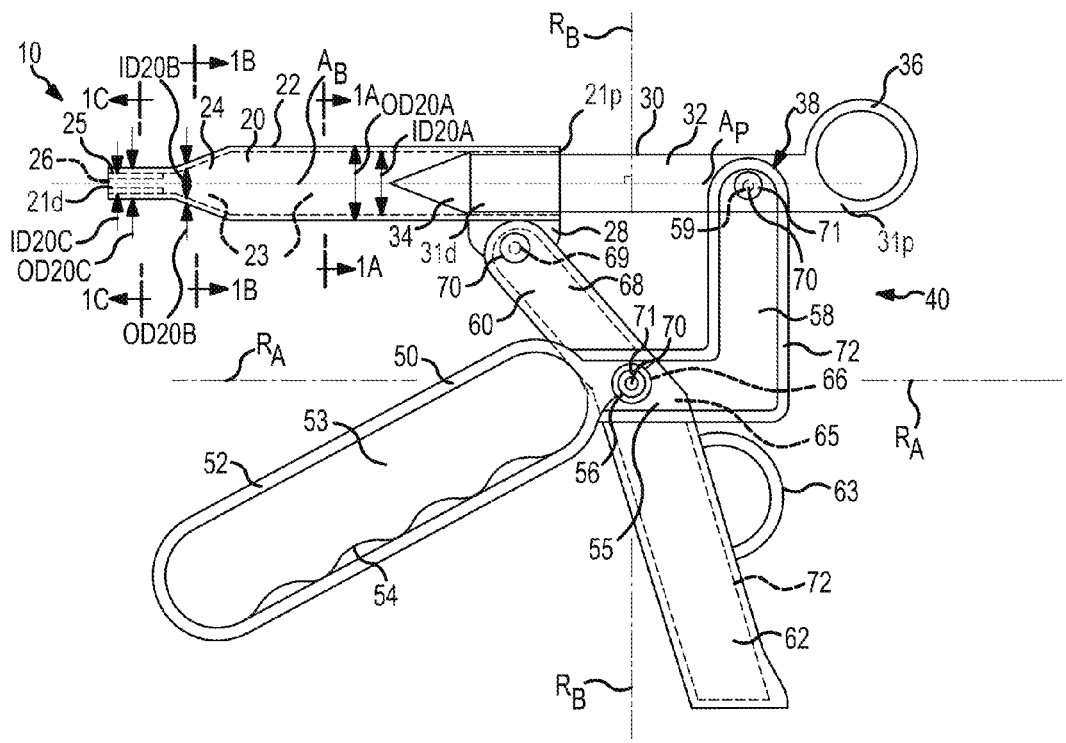
FIG. 1 is a side view of a power syringe incorporating teachings of the present invention, including a syringe barrel, a plunger that is longitudinally movable within a receptacle of the syringe barrel, and a scissor-grip handle that includes two members with three pivotal connection points, a first between a first member of the handle and the syringe barrel, a second between the second member of the handle and the plunger, and a third between the two handle members.

FIG. 1 illustrates an exemplary embodiment of a fluid delivery apparatus, or power syringe 10, incorporating teachings of the present invention. Power syringe 10 includes a barrel 20, a plunger 30 associated with barrel 20, and a scissor-grip handle 40 which causes plunger 30 to move longitudinally relative to barrel 20. One or both of barrel 20 and plunger 30 may be removable from handle 40 to facilitate the replacement of these elements and the reuse of handle 40.

Barrel 20 of power syringe 10 is an elongate member with a hollow interior extending through the length thereof. Along the majority of its length, barrel 20 is substantially uniform in both cross-sectional shape and cross-sectional dimensions. The region of barrel 20 having such substantial cross-sectional uniformity is referred to herein as body 22. As depicted, body 22 extends from a proximal end 21p of barrel 20 to a tapered section or region 24 thereof. A syringe tip 25 is located on the opposite side of tapered section 24, at the distal end 21d of barrel 20.

Figure 1A:
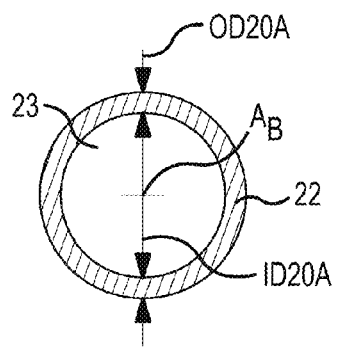
FIGS. 1A-1C are cross-sections taken along lines 1A-1A, 1B-1B, and 1C-1C, respectively, of FIG. 1.
Figure 1B:
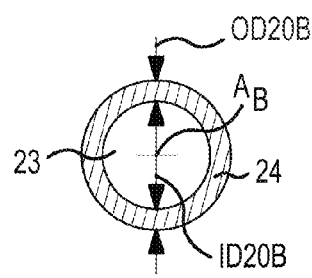
Figure 1C:
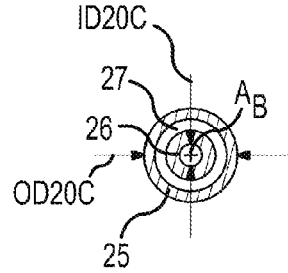

As shown in FIGS. 1-1C, the distances across opposed points of various cross-sections taken transverse to longitudinal axis $A_B$ of barrel 20 on the outer surface of barrel 20 or the outer diameter of barrel 20 are collectively referred to herein as OD20. The corresponding distances across opposed points of various cross-sections taken transverse to longitudinal axis $A_B$ on the inner surface of barrel 20 or the inner diameter of barrel 20 are collectively referred to herein as ID20.

As is depicted in FIGS. 1 and 1A, both OD20A and ID20A remain substantially the same along the substantial length of a body 22 of barrel 20. At tapered region 24, OD20 and ID20, which are respectively depicted at one location along the length of tapered region 24 as OD20B and ID20B, gradually (either linearly or along a curve) decrease from the sizes of OD20A and ID20A of body 22 to the much smaller sizes OD20C and ID20C of syringe tip 25. At syringe tip 25, the sizes of OD20C and ID20C are again substantially constant.

It is preferred that the taper of tapered region 24 occur at an angle of about 15° to longitudinal axis $A_B$ of barrel 20. Other taper angles are, however, also within the scope of the present invention.

Figure 2:
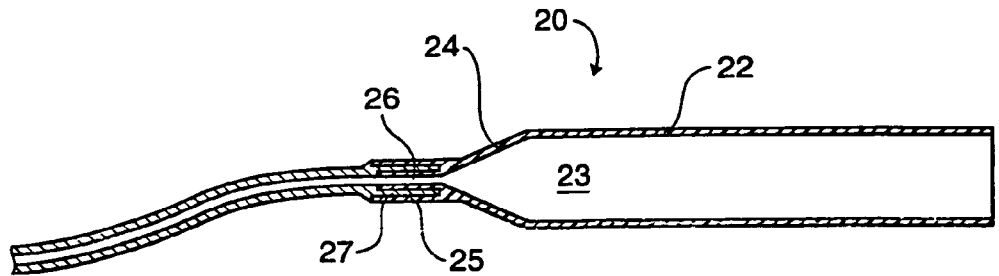
FIG. 2 is a cross-sectional representation of the syringe barrel of the power syringe of FIG. 1, illustrating the syringe barrel in an assembled relationship with a catheter.

Turning now to FIG. 2, within body 22 and tapered region 24 of barrel 20, the hollow interior thereof forms a receptacle 23. The volume of receptacle 23 is preferably suitable for the desired use of power syringe 10 (FIG. 1). For example, in applications where only small volumes of materials will be injected or aspirated with power syringe 10, barrel 20 may include a receptacle 23 with a relative small volume (e.g., 5 cubic centimeters ("cc"), 10 cc, etc.). When power syringe 10 is to be used to inject or aspirate larger volumes of materials, the volume of receptacle 23 may also be larger (e.g., 20 cc, 30 cc, 60 cc, etc.). Alternatively, receptacle 23 of barrel 20 may have other standard syringe volumes or a volume that is tailored to a specific use for power syringe 10.

The hollow interior of syringe tip 25 is referred to herein as a lumen 26. Lumen 26 may have a diameter of as small as about 1 mm (0.40 inch) or smaller. Of course, syringe tips 25 with different sizes of lumens 26 are within the scope of the present invention, as the size of a lumen 26 depends at least partially upon the gauge of a needle or the lumen size of a catheter to be coupled with syringe tip 25.

In addition, in order to facilitate the coupling of a needle or catheter with syringe tip 25, syringe tip 25 includes a coupling member 27 at or near the distal end 21d of barrel 20. Although FIG. 1 depicts coupling member 27 as including a cylindrically shaped recess that extends partially into syringe tip 25, coupling members of other configurations, including, without limitation, threaded or nonthreaded coupling members that facilitate the coupling of a needle, catheter, or other member to an outer surface of syringe tip 25, are also within the scope of the present invention.

Figure 3:
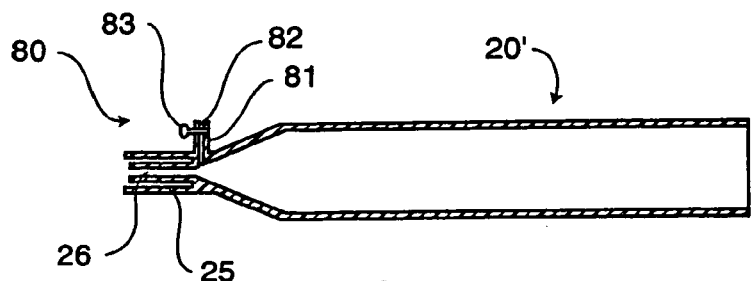
FIG. 3 is a cross-sectional representation of a variation of the syringe barrel illustrated in FIGS. 1 and 2, which includes an aspiration port that may communicate with a source or reservoir for introducing fluid into the syringe barrel upon appropriate movement of the plunger to increase the available volume within the syringe barrel.

As illustrated in FIG. 3, a variation of barrel 20' may include an aspiration port 80 proximate syringe tip 25. Aspiration port 80 facilitates the introduction of a fluid, such as a saline solution, medicine, anesthetic, indicator solution (e.g., dye, radioactive solution, radiopaque solution or x-ray contrast media, etc.), other chemical compound, or the like from an external source into receptacle 23 of barrel 20. Aspiration port 80 is depicted as comprising a cylindrical protrusion 81, which is configured to have a length of tubing coupled thereto, and a lumen 82 that extends through protrusion 81 and communicates with lumen 26 of syringe tip 25. In addition, aspiration port 80 may include a valve 83, such as a stop cock type valve, which opens and closes lumen 82. Of course, other configurations of aspiration ports are also within the scope of the present invention.

Referring again to FIG. 1, barrel 20 also includes a handle connection element 28. As depicted, handle connection element 28 extends from body 22 at proximal end 21p of barrel 20 and includes an aperture formed therethrough. The aperture is sized and configured to receive a hinge element 70 and, thus, to facilitate the connection of a member of handle 40 to barrel 20.

Figure 1D:
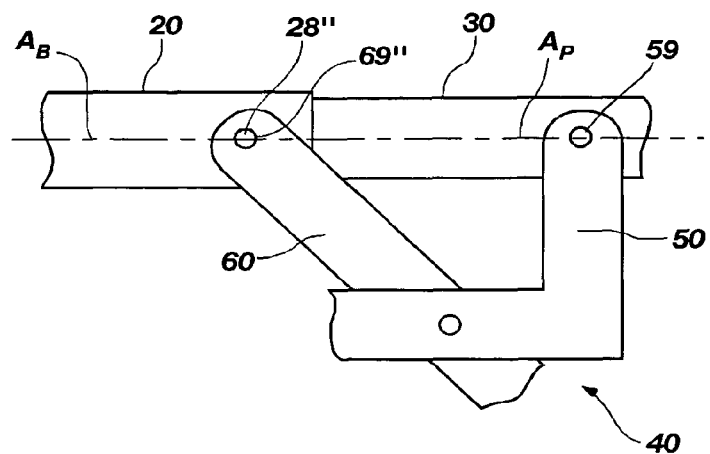
FIG. 1D illustrates a variation on the manner in which a member of a handle of the syringe of FIG. 1 may be connected to the barrel of that syringe.

Alternatively, as shown in FIG. 1D, a handle connection element 28" may include features on opposite sides of barrel 20. Such a connection point arrangement places the pivotal points that are established by connection elements 59 and 69" that are associated with handle 40 members 50 and 60, respectively, substantially in-line with axes $A_B$ of barrel 20 and $A_P$ of plunger 30.

While FIG. 1 depicts barrel 20, receptacle 23, and lumen 26 as having substantially cylindrical shapes with circular cross-sections taken transverse to a longitudinal axis $A_B$ of barrel 20, syringe barrels with any other suitable cross-sectional shapes (e.g., ovals, ellipses, polygons, etc.) are also within the scope of the present invention.

With continued reference to FIG. 1, plunger 30 is an elongate member with dimensions that permit plunger 30 to be inserted into receptacle 23 of barrel 20 through proximal end 21p thereof. Plunger 30 includes a body 32 and a head 34 at the distal end 31d of body 32. The proximal end 31p of body 32 and, thus, of plunger 30 is configured to have force applied thereto to facilitate movement of plunger 30 in both directions along a longitudinal axis $A_P$ of plunger 30.

Head 34 of plunger 30 preferably comprises a somewhat deformable, resilient member. By way of example, head 34 may be formed from silicone or any other resilient polymer (i.e., rubber) that is suitable for use in medical applications. The shape of head 34 is preferably substantially complementary to a shape of the portion of receptacle 23 of barrel 20 that is located within tapered region 24 and a portion of body 22 adjacent thereto. The size of head 34 is preferably substantially the same as or somewhat larger than the correspondingly shaped portion of receptacle 23 so as to facilitate the substantial displacement of fluid from receptacle 23 as plunger 30 is fully inserted therein.

Preferably, in order to facilitate movement of head 34 of plunger 30 along the full length of receptacle 23, the length of plunger 30 is greater than the combined lengths of body 22 and tapered region 24 of barrel 20. Of course, in order to apply the amount of force necessary to move plunger 30 through the length of receptacle 23, body 32 of plunger 30 is preferably formed from a more rigid material than that of head 34. Accordingly, head 34 preferably includes a receptacle (not shown) that is configured to receive a corresponding head connection protrusion (not shown) at the distal end of body 32, as known in the art.

Proximal end 31p of plunger 30 includes a handle connection element 38. Handle connection element 38 includes an aperture formed through body 32 of plunger 30 at a location that facilitates the pivotal connection of a member of handle 40 thereto by way of a hinge element 70.

In addition, proximal end 31p of plunger 30 may include a secondary movement element 36, such as a loop or another member by which an individual may cause plunger 30 to move in one or both directions along longitudinal axis $A_P$ thereof.

Still referring to FIG. 1, handle 40 includes two elongate members, a first member 50 and a second member 60. First member 50 and second member 60 are pivotally connected with one another in a manner that, along with the shapes of first and second members 50 and 60, provides leverage so as to decrease the amount of force that must be exerted by an individual's hand to move plunger 30 relative to barrel 20.

First member 50, which is configured to be held with an individual's fingers, includes a gripping end 52 and a plunger attachment end 58. In addition, first member 50 includes pivotal connection element 56 positioned at a central region 55 thereof, which is located substantially centrally along the length thereof, to facilitate connection of first member 50 to second member 60 of handle 40. Pivotal connection element 56 includes an aperture that has a circular shape and that receives a hinge element 70, or pivot pin, which, in turn, connects first member 50 and second member 60 to one another.

As shown, first member 50 includes an elongated loop 53 along gripping end 52, through which an individual's fingers may be inserted. Alternatively, or in addition to loop 53, gripping end 52 may include a finger grip 54 that is contoured so as to comfortably receive the fingers of an individual.

Plunger attachment end 58 includes (e.g., terminates at) a plunger connection element 59 that facilitates the pivotal connection of first member 50 to the corresponding handle connection element 38 of plunger 30. Plunger connection element 59 may comprise an aperture that is configured to receive hinge element 70. First member 50 and plunger 30 are pivotally connected to one another by positioning plunger attachment end 58 against the appropriate location of plunger 30 with plunger connection element 59 and an aperture (not shown) of handle connection element 38 in alignment. A single hinge element 70 is then inserted through both plunger connection element 59 and the noted aperture of handle connection element 38. Hinge element 70 preferably includes an enlarged head 71 at each end thereof to maintain the assembled, pivotal relationship of plunger 30 and first member 50. Of course, other known types of pivotal connection arrangements between plunger 30 and first member 50 and their corresponding elements are also within the scope of the present invention.

First member 50 is bent, or angled, at some point along the length thereof, between gripping end 52 and plunger attachment end 58, to at least partially provide the desired amount of leverage for forcing plunger 30 to move longitudinally through receptacle 23 of barrel 20. As shown in FIG. 1, first member 50 is angled at two locations, a first of which is located between gripping end 52 and central region 55 and a second of which is located between central region 55 and plunger attachment end 58. Although FIG. 1 depicts gripping end 52 and central region 55 as being oriented at an angle of about 140° relative to one another and central region 55 and plunger attachment end 58 as being oriented at an angle of about 90° relative to one another, other angles and bend locations are also within the scope of the present invention.

Still referring to FIG. 1, second member 60 of handle 40 is an elongate member that is configured to be held by an individual's palm or thumb. Second member 60 includes a gripping end 62 and a barrel attachment end 68, as well as a central region 65 located between gripping end 62 and barrel attachment end 68.

Gripping end 62 of second member 60 may include a thumb loop 63 through which the thumb of an individual using power syringe 10 may be inserted.

Central region 65 of second member 60 includes a pivotal connection element 66 that corresponds to pivotal connection element 56 of first member 50. Pivotal connection element 66 may comprise an aperture formed through central region 65 and configured to receive hinge element 70. Upon properly orienting first member 50 and second member 60 relative to one another in an assembled relationship thereof and aligning the aperture of first member 50 with the aperture of second member 60, hinge element 70 may be inserted through the apertures to pivotally connect first and second members 50 and 60 to one another. Hinge element 70 preferably includes an enlarged head 71 at each end thereof to maintain the assembled, pivotal relationship of first member 50 and second member 60.

Figure 4:
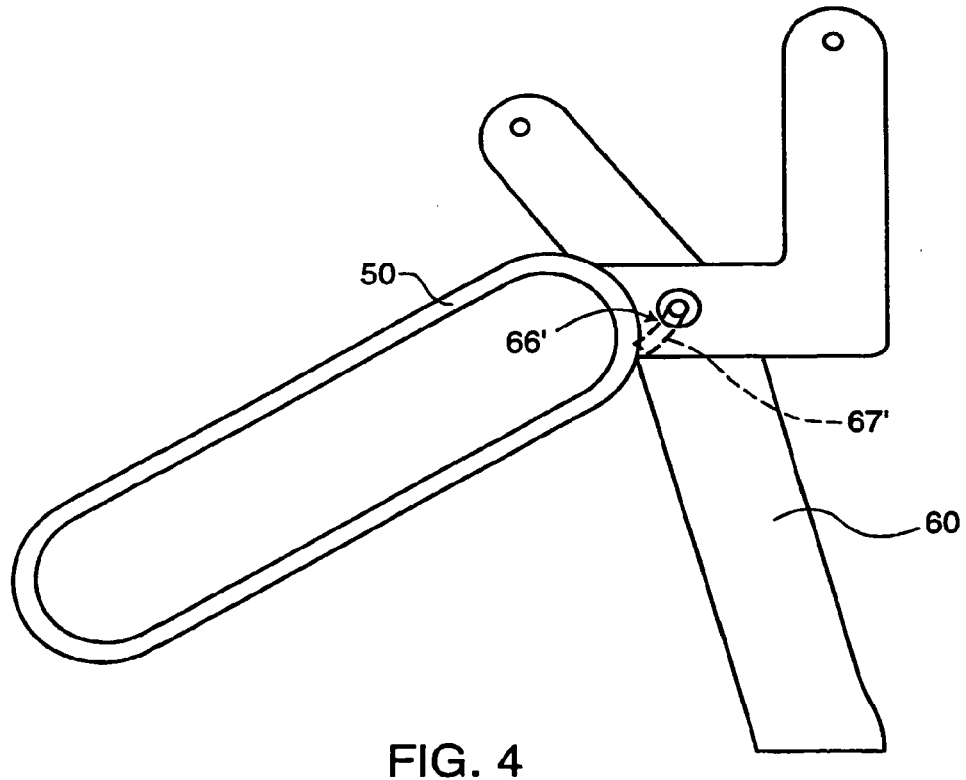
FIG. 4 is a side view that depicts a variation of the handle of FIG. 1, with one of the first and second members including an arcuate slot through which a movable connection member on the other of the two members moves when the handle members are moved relative to one another.

Alternatively, as depicted in FIG. 4, a variation of pivotal connection element 66' may comprise an arcuate slot 67', along the length of which pivotal connection element 56 may move as first and second members 50 and 60 are moved toward or apart from one another.

Figure 5:
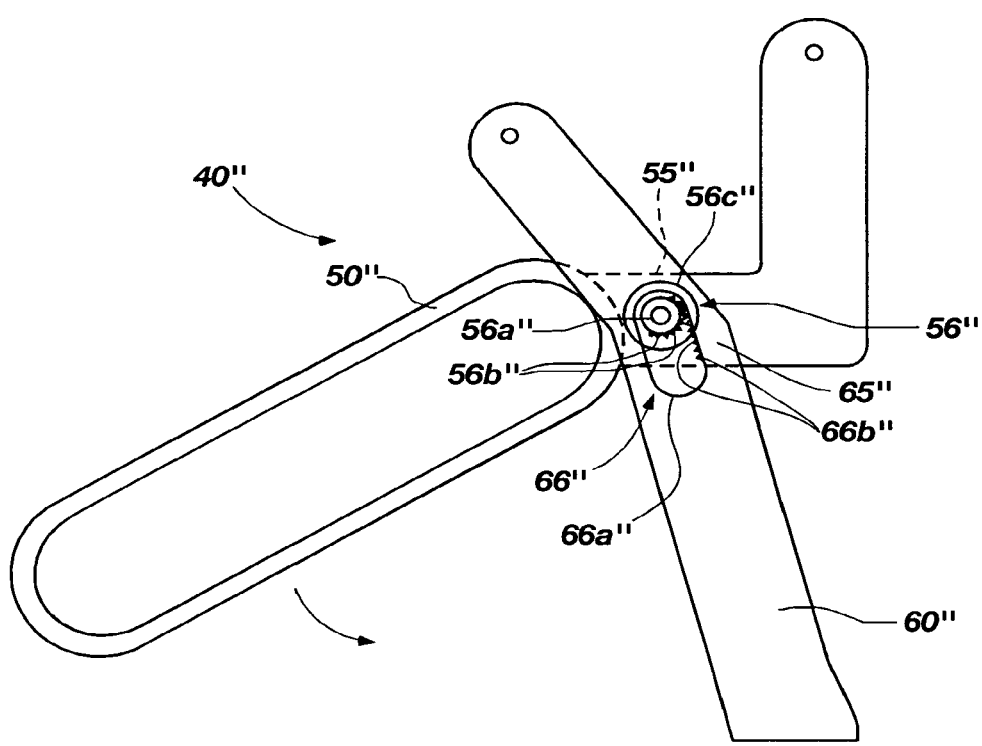
FIG. 5 is a side view that depicts another variation of the handle of FIG. 1, wherein one of the first and second handle members includes a partial gear member and the other of the first and second handle members includes an elongated slot with teeth along an edge thereof for receiving teeth of the partial gear member upon movement of the two handle members relative to one another.

As another alternative, shown in FIG. 5, a handle 40" of a power syringe according to the present invention includes another embodiment of connection element 56" on central region 55" of first member 50" and another, corresponding embodiment of pivotal connection element 66" on central region 65" of second member 60". Connection element 56", which protrudes from central region 55" and is fixed in relation thereto, includes a cylindrical section 56a", a series of adjacent teeth 56b" protruding from at least a portion of the curved surface of cylindrical section 56a", and an enlarged retention head 56c" adjacent cylindrical section 56a", opposite from the remainder of first member 50". The distance that cylindrical section 56a" protrudes from central region 55" of first member 50" is preferably slightly larger than the thickness of second member 60".

The corresponding pivotal connection element 66" of second member 60" comprises an elongated slot 66a" with a series of adjacent teeth 66b" protruding from at least a portion of an edge along the length of slot 66a". Teeth 66b" are configured and positioned complementarily to teeth 56b" of connection element 56" such that teeth 56b" and teeth 66b" cooperate by mutually engaging each other upon rotation of cylindrical section 56a" relative to slot 66a". The width of slot 66a" is preferably slightly larger than the diameter of cylindrical section 56a" of pivotal connection element 56" so as to substantially prevent side-to-side movement of pivotal connection element 56" relative to pivotal connection element 66". Consequently, the relative movement of pivotal connection elements 56" and 66" with respect to one another is substantially confined on the direction in which pivotal connection element 66" extends, which, as illustrated, is along the length of second member 60". Thus, when first and second handle members 50" and 60" are forced toward one another, pivotal connection element 56" rotates relative to pivotal connection element 66" and moves downward through slot 66a" of pivotal connection element 66". Conversely, when first and second handle members 50" and 60" are forced apart from one another, pivotal connection element 56" rotates and moves in the opposite direction relative to pivotal connection element 66".

Referring again to FIG. 1, handle 40 may additionally include a resilient element (e.g., a spring) may be associated with first and second members 50 and 60 (e.g., at or near hinge element 70) in such a way as to force first and second members 50 and 60 apart from one another when they are not being held together.

When first and second members 50 and 60, or variations thereof, have been properly assembled with one another, it is preferred that practically any adult user be able to properly position their fingers on gripping end 52 and their thumb or palm against gripping end 62 while gripping ends 52 and 62 are spaced a maximum distance apart from one another with head 34 of plunger located at proximal end 21p of barrel 20.

Barrel attachment end 68 includes (e.g., terminates at) a barrel connection element 69 that facilitates the pivotal connection of second member 60 to the corresponding handle connection element 28 of barrel 20. As depicted, barrel connection element 69 comprises an aperture that is configured to receive a hinge element 70. Second member 60 and barrel 20 are pivotally connected to one another by properly positioning barrel attachment end 68 and handle connection element 28 against one another, with the apertures thereof in alignment, and inserting a single hinge element 70 through both barrel connection element 69 and handle connection element 28. Hinge element 70 preferably includes an enlarged head 71 at each end thereof to maintain the assembled, pivotal relationship of barrel 20 and second member 60. Of course, other known types of pivotal connection arrangements between barrel 20 and second member 60 and their corresponding elements are also within the scope of the present invention.

Second member 60 of handle 40 may be bent, or angled, to increase the leverage provided by first member 50 and the scissor-like arrangement of first member 50 and second member 60. As illustrated, second member 60 is bent at central region 65 thereof to position gripping end 62 in proximity to gripping end 52 of first member 50 when first member 50 and second member 60 are in an appropriate assembled relationship. With further regard to the noted scissor-like arrangement between the first member 50 and second member 60, the side view of FIG. 1 shows a reference axis $R_A$ that extends through the hinge element 70 (that pivotally interconnects the first member 50 and the second member 60) and that is parallel to both the longitudinal axis $A_B$ of barrel 20 and the longitudinal axis $A_P$ of plunger 30. Note that both plunger attachment end 58 (of first member 50) and barrel attachment end 68 (of second member 60) each extend relative to the hinge element 70 (between first member 50 and second member 60) onto one side of this reference axis $R_A$ (on the side that is "above" the reference axis $R_A$ in the side view of FIG. 1), and that both gripping end 52 (of first member 50) and gripping end 62 (of second member 60) each extend relative to the hinge element 70 (between first member 50 and second member 60) onto the opposite side of this reference axis $R_A$ (on the side that is "below" the reference axis $R_A$ in the side view of FIG. 1). With further regard to the noted scissor-like arrangement between the first member 50 and second member 60, the side view of FIG. 1 shows a reference axis $R_B$ that extends through the hinge element 70 (that pivotally interconnects the first member 50 and the second member 60) and that is perpendicular to both the longitudinal axis $A_B$ of barrel 20 and the longitudinal axis $A_P$ of plunger 30.

Of course, one or both of first member 50 and second member 60 may include reinforcement ribs 72 or other reinforcement structures along at least a portion of the length thereof. As depicted, reinforcement ribs 72 are positioned along the edges of first member 50 and second member 60. Reinforcement ribs 72 may be positioned to prevent side-to-side bending of first member 50 or second member 60 during use of handle 40 to move plunger 30 relative to barrel 20.

Figure 6A:
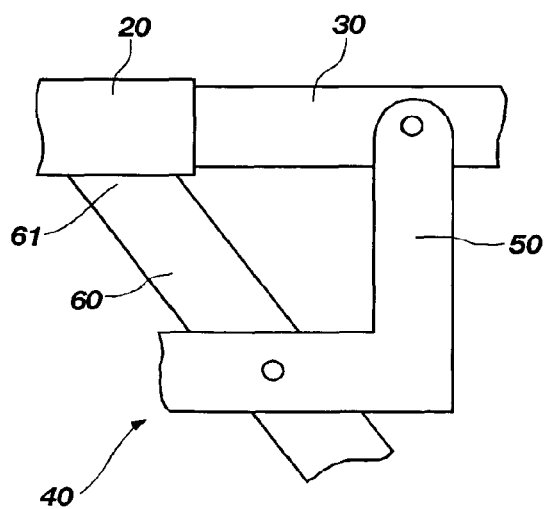
FIG. 6A depicts a power syringe with a fixed connection between a barrel and its corresponding handle.
Figure 6B:
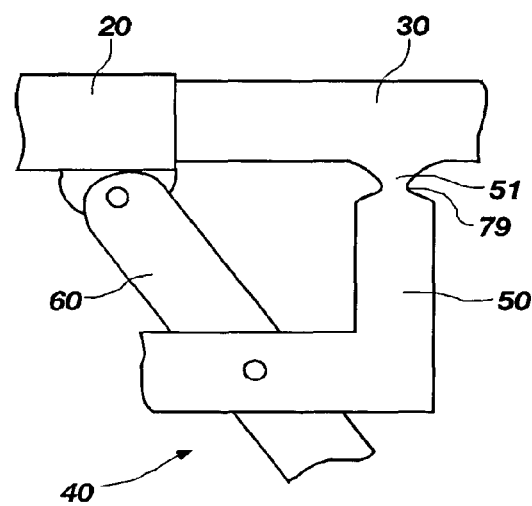
FIG. 6B illustrates a power syringe with a fixed connection between a plunger and its corresponding handle.

FIGS. 6A and 6B illustrate variations of power syringe 10 (FIG. 1), in which first member 50 and second member 60 of handle 40 are pivotally connected to one another, but at least one connection point between an end of a member 50, 60 of handle 40 and barrel 20 or plunger 30 does not pivot. In FIG. 6A, a connection point 61 between an end of member 60 and barrel 20 does not pivot. In FIG. 6B, a connection point 51 between an end of member 50 and plunger 30 does not pivot. While connection points 61 and 51 do not pivot, the ends of members 60 and 50 may still be nonrigidly (e.g., flexibly) connected with barrel 20 and plunger 30, respectively (e.g., by way of a flexible connecting material, an integral region of thickness 79, etc.). Alternatively, at least one connection point 61, 51 may be substantially rigid. Although FIGS. 6A and 6B illustrate only a single non-pivoting connection point 61, 51, a power syringe may include two non-pivoting connection points 61, 51.

Figure 7:
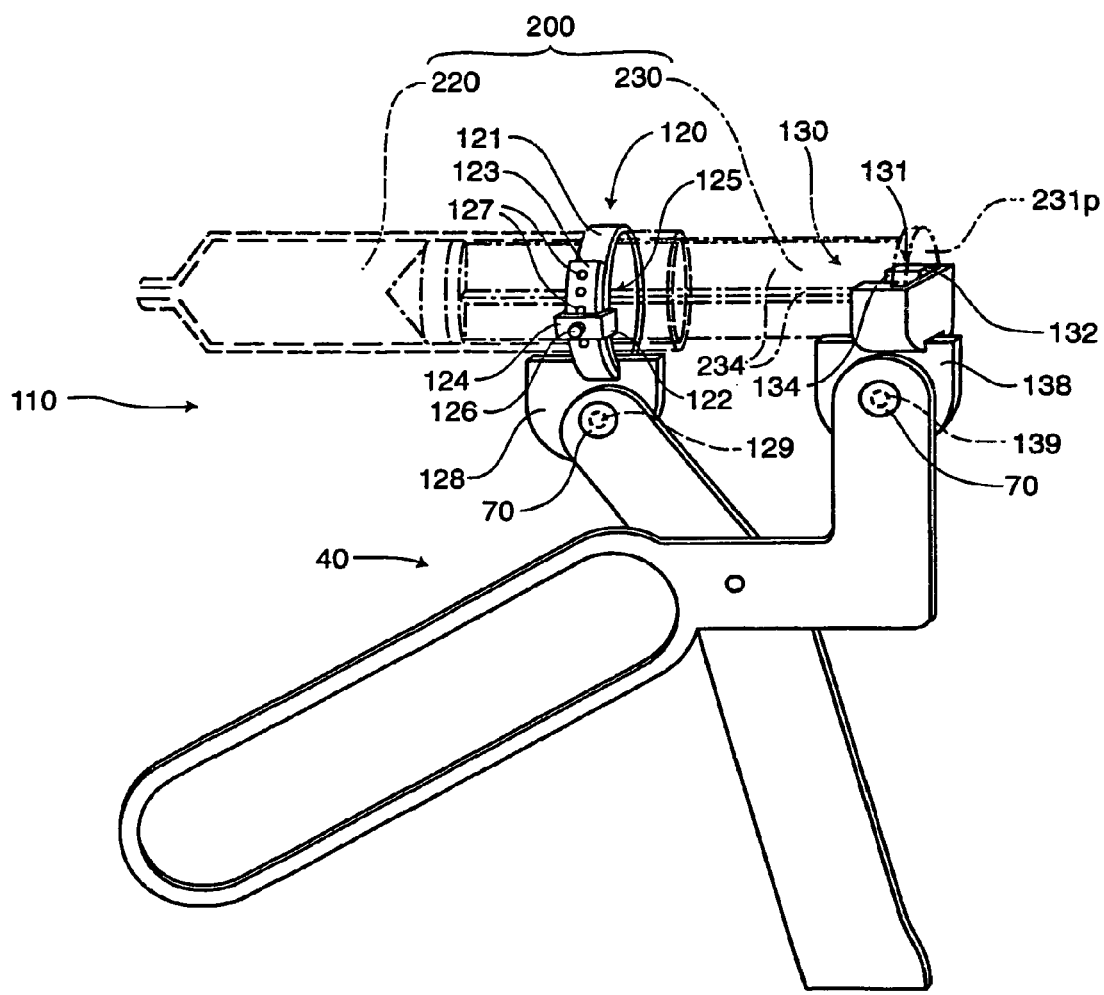
FIG. 7 is a side view of an alternative embodiment of a power syringe incorporating teachings of the present invention, wherein a disposable syringe barrel and plunger may be assembled and used with a reusable injection/aspiration handle.

Turning to FIG. 7, another embodiment of a power syringe 110 according to the present invention is illustrated. Power syringe 110 includes a scissor-grip handle 40, a barrel retaining member 120 pivotally secured to a second member 60 of handle 40, and a plunger biasing member 130 pivotally secured to a first member 50 of handle 40.

Barrel retaining member 120 is configured to engage and retain at least a portion of the barrel 220 of a syringe 200. The depicted, exemplary embodiment of barrel retaining member 120 includes a flexible, elongate member 121 with a receptacle 124 at one end 122 thereof. Receptacle 124 is configured to receive the other end 123 of elongate member 121, as well as to facilitate the movement of a received portion of elongate member 121 therethrough. When receiving end 123 of elongate member 121 has been inserted into or through receptacle 124, barrel retaining member 120 takes on an annular configuration, forming a barrel receptacle 125 that may receive a portion of barrel 220 of syringe 200. As elongate member 121 moves through receptacle 124, the size of barrel receptacle 125 changes. The position of a portion of elongate member 121 extending through receptacle 124 may be maintained by way of a size adjustment member 126 (e.g., a screw, a spring-biased pin, etc.) that protrudes into receptacle 124 to engage the portion of elongate member 121 therein. Elongate member 121 may also include retention recesses 127 (e.g., grooves, slots, etc.) that are oriented along the length of elongate member 121 and that are configured to receive an interior end of size adjustment member 126 so as to further maintain the position of elongate member 121 relative to receptacle 124 and, thus, the size of barrel receptacle 125.

Barrel retaining member 120 also includes a handle connection element 128 which extends from elongate member 121 and includes an aperture 129 therethrough. Aperture 129 is sized and configured to receive a hinge element 70 and, thus, to facilitate connection of a member of handle 40 to barrel retaining member 120.

Of course, other embodiments of barrel retaining members, which may be configured to receive a variety of different sizes of syringes or single syringe sizes, are also within the scope of the present invention.

With continued reference to FIG. 7, an exemplary embodiment of plunger biasing member 130 is configured to receive, retain, and apply force to a proximal end 231p of a plunger 230 of syringe 200. Accordingly, the illustrated plunger biasing retaining member 130 includes a plunger receiving portion 131 that is configured to receive and apply pressure to proximal end 231p of plunger 230. As illustrated, plunger receiving portion 131 includes a receptacle 132 that is configured to receive at least a portion of the disk-shaped proximal end 231p of a conventionally configured syringe plunger 230. In addition, plunger biasing retaining member 130 includes a slot 134 that is continuous with receptacle 132 and that is positioned and sized to receive a portion of at least one of the support ribs 234 of a conventionally configured syringe plunger 230. As depicted, proximal end 231p is substantially completely received within receptacle 132. Accordingly, slot 134 may include a narrow bottom section that receives a single, vertically oriented support rib 234 and a wider top section that receives opposed, horizontally oriented support ribs 234.

A handle connection element 138 is positioned adjacent to (beneath) plunger receiving portion 131 and includes an aperture 139 that is configured to receive a portion of a hinge element 70 and to pivotally connect plunger biasing member 130 to first member 50 of handle 40.

Handle 40 of power syringe 110 may be configured as described previously herein.

Figure 8:
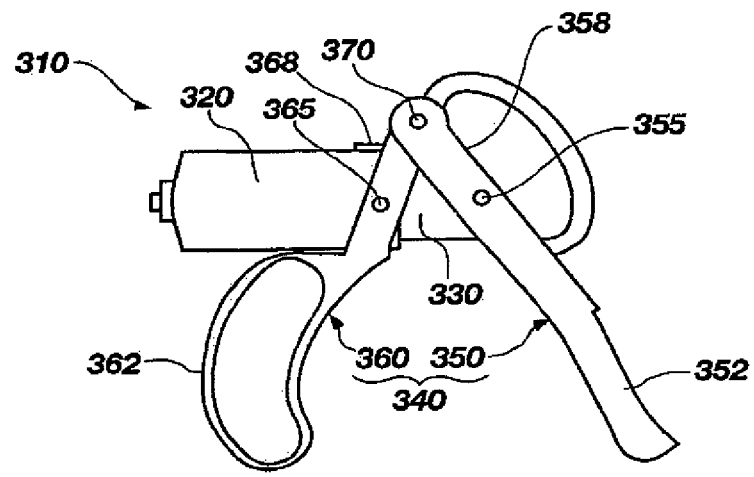
FIGS. 8 and 9 show alternative embodiments of syringes that incorporate teachings of the present invention.
Figure 9:
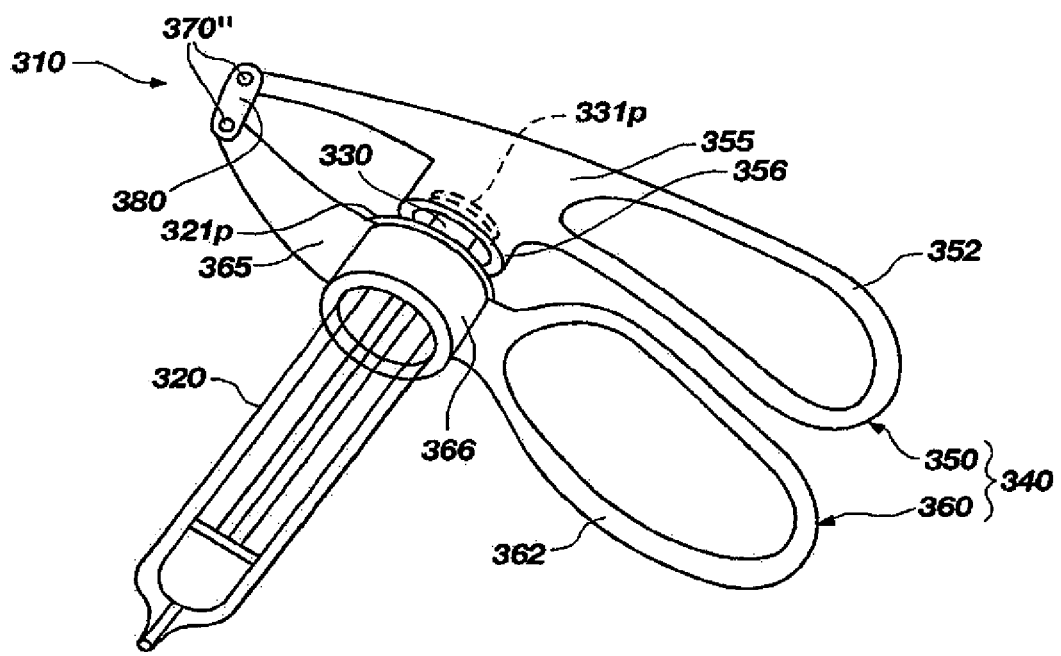

Examples of another embodiment of power syringe 310 according to the present invention are shown in FIGS. 8 and 9. Power syringe 310 includes a handle 340 with two members 350 and 360 that include ends 358 and 368 that are pivotally connected to one another, such as with the illustrated pivot hinge 370. As shown, pivot hinge 370 is located on an opposite side of a barrel 320 and plunger 330 of power syringe 310 than gripping ends 352 and 362 of members 350 and 360, respectively.

An intermediate portion 355 of member 350, which is the member of handle 340 that is proximal relative to a user of power syringe 310, is associated with plunger 330. As shown, member 350 may include a capture element 356, or connection point, associated with (e.g., connected to) a proximal end 331p of plunger 330. Capture element 356 may be pivotally (see FIG. 8) or nonpivotally secured to proximal end 331p. Alternatively, capture element 356 may be configured to receive proximal end 331p of plunger 330 (see FIG. 9), in which case the configuration (e.g., have dimensions, a shape, a compressible and resilient element, etc.) of capture element 356 may allow for at least some movement, or "play," of proximal end 331p as members 350 and 360 of handle 340 are moved toward or away from one another.

An intermediate portion 365 of member 360, which is the member that is distal relative to a user of power syringe 310, is associated with barrel 320 at capture element 366. Capture element 366 receives at least a proximal end 321p of barrel 320, which may be in a longitudinally or axially fixed position relative to capture element 366, or may slide through capture element 366. Capture element 366 may be configured (e.g., have dimensions, a shape, a compressible and resilient element, etc.) that accommodates some movement of barrel 320 relative to member 360 (see FIG. 9). Alternatively, or in addition, capture element 366 may pivot (see FIG. 8) or facilitate pivoting of barrel 320 relative to member 360 as members 350 and 360 of handle 340 are moved toward or away from one another.

Optionally, as shown in FIG. 9, a connection element 380 between members 350 and 360 of handle 340 may include two or more pivot points 370". Such arrangement may facilitate a more rigid connection between at least one of member 350 and plunger 330 and member 360 and barrel 320.

While the various elements of a power syringe according to the present invention (e.g., power syringe 10) may be manufactured from any suitable material or materials, it is preferred that each of the elements of the power syringe be formed by injection molding processes so as to afford low manufacturing cost and, consequently, to facilitate single-use, or disposability, of the power syringe. For the more rigid elements, which, in power syringe 10 (FIG. 1) include substantially all of the elements thereof with the exception of head 34 of plunger 30, polycarbonates, such as LEXAN®, manufactured by General Electric, or MAKROLON®, manufactured by Miles Chemicals, may be used. Of course, other medical grade plastics having properties (strength, rigidity, structural integrity, ability to be adequately sterilized while maintaining other desired properties, etc.) that are suitable for the desired functions of the various elements of a power syringe may be used to form those elements. Alternatively, suitable metals, such as stainless steel, which have the desired properties may be used to form one or more of the elements of a power syringe that incorporates teachings of the present invention. These configurations are not, however, requirements, nor are the materials or method of fabrication are not critical to any inventive aspect disclosed herein.

Figure 10:
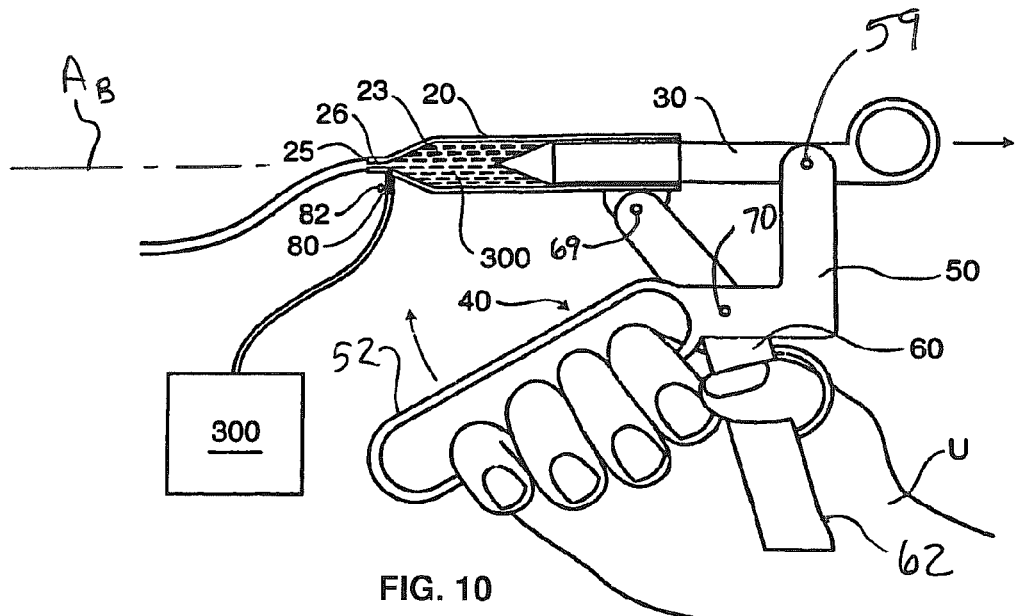
FIGS. 10-10B are schematic representations of use of a power syringe incorporating teachings of the present invention.
Figure 10A:
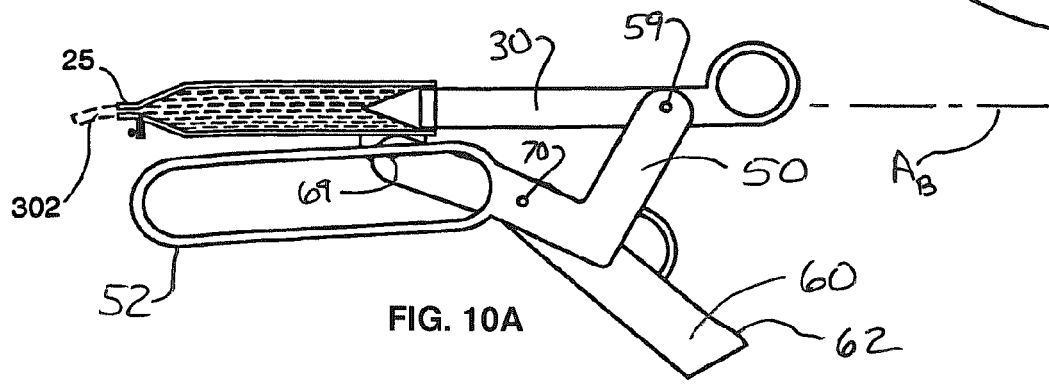
Figure 10B:
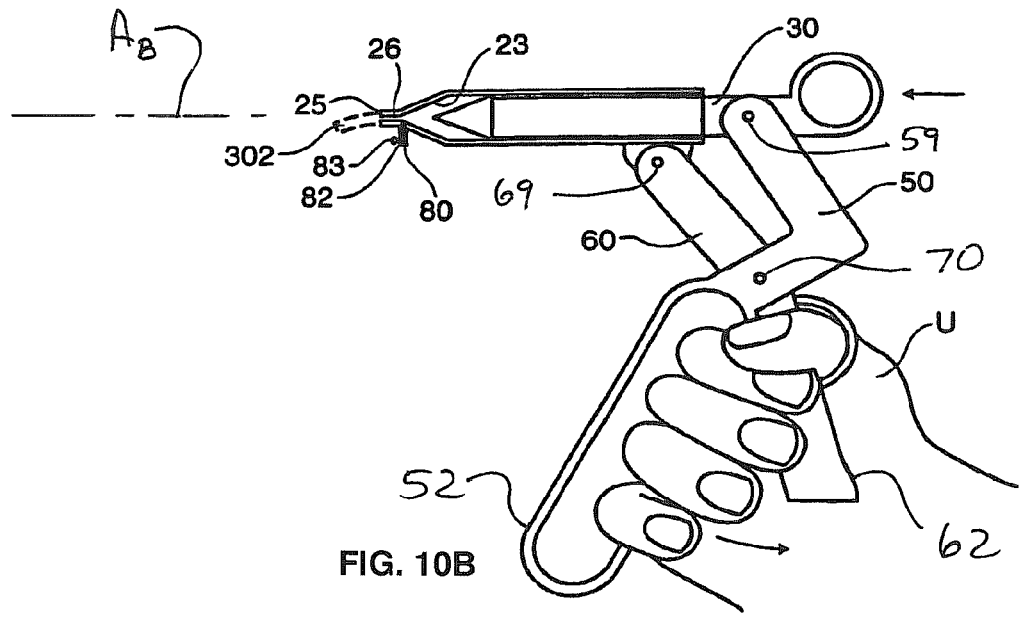

Turning now to FIGS. 10-10B, an example of the use of a power catheter incorporating teachings of the present invention is illustrated.

FIG. 10 illustrates the introduction of a fluid 300 into receptacle 23 of barrel 20 through either lumen 26 of syringe tip 25 (FIGS. 1 and 2) or lumen 82 of aspiration port 80 (FIG. 3) by drawing plunger 30 outwardly (proximally) through receptacle 23. Note the spacing between the plunger connection element 59 (between plunger 30 and first member 50) and the barrel connection element 69 (between barrel 20 and second member 60), measured along an axis that is parallel to the longitudinal axis $A_B$ of barrel 20. Also note the spacing between gripping end 52 (first member 50) and gripping end 62 (second member 60), measured along an axis that is parallel to the longitudinal axis $A_B$ of barrel 20. Plunger 30 may be drawn outwardly through receptacle 23 by a user U forcing first and second members 50 and 60 of handle 40 apart from one another and as shown in FIG. 10A. As plunger 30 is drawn outwardly through receptacle 23, the available volume of receptacle 23 (i.e., that located distally relative to head 34 of plunger 30) increases and a negative pressure is created within receptacle 23. This negative pressure forces fluid 300 to enter receptacle 23. As depicted, fluid 300 is a liquid, such as a medicine, an anesthetic, a dye, or another chemical compound. Alternatively, fluid 300 may comprise a gas, air, or another mixture of gases. In any case, note the increase in the spacing between the plunger connection element 59 (between plunger 30 and first member 50) and the barrel connection element 69 (between barrel 20 and second member 60), measured along an axis that is parallel to the longitudinal axis $A_B$ of barrel 20 and progressing from the configuration of FIG. 10 to the configuration of FIG. 10A. Also note the increase in the spacing between gripping end 52 (first member 50) and gripping end 62 (second member 60), measured along an axis that is parallel to the longitudinal axis $A_B$ of barrel 20 and progressing from the configuration of FIG. 10 to the configuration of FIG. 10A.

As shown in FIG. 10A, syringe tip 25 may be coupled to a known infusion or injection apparatus 302, shown in phantom, such as a catheter or a hypodermic needle. Infusion or injection apparatus 302 comprises a conduit which facilitates the introduction of fluid 300 into the body of an individual.

In FIG. 10B, as user U forces first member 50 and second member 60 toward one another, plunger 30 is forced inwardly (i.e., distally) through receptacle 23, decreasing the available volume within receptacle 23 and creating an increase in pressure therein. This increase in pressure within receptacle 23 forces fluid 300 out of receptacle 23 through lumen 26 of syringe tip 25, through infusion or injection apparatus 302, and into the body of the individual. With valve 83 in a closed position or orientation, fluid 300 is prevented from escaping through lumen 82 of aspiration port 80 as the pressure within receptacle 23 is being increased. The amount of fluid introduced into the individual's body may be controlled by controlling the distance first and second members 50 and 60 are forced together. In any case, note the decrease in the spacing between the plunger connection element 59 (between plunger 30 and first member 50) and the barrel connection element 69 (between barrel 20 and second member 60), measured along an axis that is parallel to the longitudinal axis $A_B$ of barrel 20 and progressing from the configuration of FIG. 10A to the configuration of FIG. 10B. Also note the decrease in the spacing between gripping end 52 (first member 50) and gripping end 62 (second member 60), measured along an axis that is parallel to the longitudinal axis $A_B$ of barrel 20 and progressing from the configuration of FIG. 10A to the configuration of FIG. 10B.

Returning reference to FIG. 1, the three-pivot-point configuration of handle 40 provides sufficient leverage that the force applied by a single hand of a user will be translated into an adequate amount of force upon plunger 30 and within receptacle 23 to force even relatively high viscosity fluids into and out of receptacle 23. Moreover, the configurations of members 50 and 60 of handle 40 facilitate gripping thereof with a single hand, the fine motor skills of which can be used in such a way as to precisely control the amount of fluid being introduced into or discharged from receptacle 23 of syringe barrel 20.

Power catheters incorporating teachings of the present invention may be used in a variety of different procedures, including, without limitation, injecting medicines or drugs into an individual, either through a hypodermic needle into the individual's tissues or intravenously (i.e., into a vein of an individual), introducing dyes or other indicator solutions into the bloodstream of a particular location of individual's body (e.g., in angiography), introducing a gas, air, or another gas mixture into an angioplasty balloon to inflate the same in a process which is typically referred to as percutaneous transluminal coronary angioplasty ("PTCA"), or obtaining samples of blood, other fluids, or tissues (e.g., with a biopsy needle or other biopsy instrument). A power syringe according to the present invention may also be used to remove air or gas from such a balloon or to obtain samples from the body of an individual, as well as in other applications where syringes have been used.

Although the foregoing description contains many specifics, these should not be construed as limiting the scope of the present invention, but merely as providing illustrations of some exemplary embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions, and modifications to the invention, as disclosed herein, which fall within the meaning and scope of the claims are to be embraced thereby.

What is claimed is:

1. A hand-held fluid delivery apparatus, comprising:
   a syringe comprising:
      a syringe barrel comprising a fluid receptacle; and
      a plunger disposable within the fluid receptacle of the syringe barrel and moveable along a length of the barrel along a longitudinal axis; and
   a handle comprising:
      a first member comprising a first gripping end and a plunger attachment end pivotally connected directly to the plunger;
      a second member comprising a second gripping end and a barrel attachment end pivotally connected directly to the syringe barrel; and
      a hinge pivotally connecting the first and second members of the handle at an intermediate location of each of the first and second members where the first and second members cross one another, the first and second members being assembled with one another and with the syringe in a manner that enables a single hand of a user to simultaneously grip both the first and second gripping ends, wherein movement of the first and second gripping ends of the first and second members toward one another displaces the plunger relative to the syringe barrel in a direction that reduces an available volume of the fluid receptacle to discharge fluid from the syringe barrel, causes the plunger attachment end of the first member to pivot relative to the plunger, and causes the barrel attachment end of the second member to pivot relative to the syringe barrel.

2. The hand-held fluid delivery apparatus of claim 1, wherein the syringe and handle are configured for disposability.

3. The hand-held fluid delivery apparatus of claim 1, wherein the first and second gripping ends each extend relative to the hinge onto one side of a reference axis that extends through the hinge and that is parallel with the longitudinal axis in a side view of the hand-held fluid delivery apparatus, and wherein the plunger attachment end and barrel attachment end each extend relative to the hinge onto an opposite side of the reference axis in the side view of the hand-held fluid delivery apparatus.

4. The hand-held fluid delivery apparatus of claim 1, wherein the syringe barrel comprises a syringe tip, and wherein the hand-held syringe further comprises one of a catheter and a needle connected to the syringe tip to accept a fluid discharge from the syringe barrel as the plunger is advanced through the fluid receptacle.

5. A hand-held fluid delivery apparatus, comprising:
   a syringe comprising:
      a syringe barrel comprising a fluid receptacle; and
      a plunger disposable within the fluid receptacle of the syringe barrel and moveable along a length of the barrel along a longitudinal axis;
   a handle comprising:
      a first member comprising a first gripping end and a plunger attachment end;
      a second member comprising a second gripping end and a barrel attachment end; and
      a hinge pivotally connecting the first and second members of the handle at an intermediate location of each of the first and second members where the first and second members cross one another;
   a single hinge element that pivotally connects the plunger with the plunger attachment end of the first member of the handle; and
   a single hinge element that pivotally connects the syringe barrel with the barrel attachment end of the second member of the handle, the first and second members being assembled with one another and with the syringe in a manner that enables a single hand of a user to simultaneously grip both the first and second gripping ends, wherein movement of the first and second gripping ends of the first and second members toward one another displaces the plunger relative to the syringe barrel in a direction that reduces an available volume of the fluid receptacle to discharge fluid from the syringe barrel, causes the plunger attachment end of the first member to pivot relative to the plunger, and causes the barrel attachment end of the second member to pivot relative to the syringe barrel.

6. The hand-held fluid delivery apparatus of claim 5, wherein the first gripping end of the first member is configured to be held by a first part of a user's hand, wherein the second gripping end of the second member is configured to be held by a second part of the user's hand, wherein the first and second gripping ends of the first and second members, respectively, each extend relative to the hinge onto one side of a first reference axis that extends through the hinge and that is parallel with the longitudinal axis in a side view of the hand-held fluid delivery apparatus, and wherein the plunger attachment end and the barrel attachment end of the first and second members, respectively, each extend relative to the hinge onto an opposite side of the first reference axis in the side view of the hand-held fluid delivery apparatus.

7. The hand-held fluid delivery apparatus of claim 6, wherein a second reference axis is perpendicular to the first reference axis and extends through the hinge between the first and second members of the handle in the side view of the hand-held fluid delivery apparatus, wherein the first gripping end of the first member and the second gripping end of the second member are positioned on opposite sides of the second reference axis in the side view of the hand-held fluid delivery apparatus, and wherein the single hinge element that pivotally connects the plunger with the plunger attachment end of the first member of the handle and the single hinge element that pivotally connects the syringe barrel with the barrel attachment end of the second member of the handle are positioned on opposite sides of the second reference axis in the side view of the hand-held fluid delivery apparatus.

8. The hand-held fluid delivery apparatus of claim 5, wherein a second reference axis is perpendicular to the longitudinal axis and extends through the hinge between the first and second members of the handle in a side view of the hand-held fluid delivery apparatus, wherein the first gripping end of the first member and the second gripping end of the second member are positioned on opposite sides of the second reference axis in the side view of the hand-held fluid delivery apparatus, and wherein the single hinge element that pivotally connects the plunger with the plunger attachment end of the first member of the handle and the single hinge element that pivotally connects the syringe barrel with the barrel attachment end of the second member of the handle are positioned on opposite sides of the second reference axis in the side view of the hand-held fluid delivery apparatus.

9. The hand-held syringe of claim 5, wherein a perpendicular reference axis extends through the hinge and is perpendicular to the longitudinal axis in a side view of the hand-held fluid delivery apparatus, and wherein the handle is configured to simultaneously move the syringe barrel and the plunger relative to the perpendicular reference axis.

10. The hand-held fluid delivery apparatus of claim 5, wherein the syringe and handle are configured for disposability.

11. The hand-held fluid delivery apparatus of claim 5, wherein the first and second gripping ends each extend relative to the hinge onto one side of a reference axis that extends through the hinge and that is parallel with the longitudinal axis in a side view of the hand-held fluid delivery apparatus, and wherein the plunger attachment end and barrel attachment end each extend relative to the hinge onto an opposite side of the reference axis in the side view of the hand-held fluid delivery apparatus.

12. The hand-held fluid delivery apparatus of claim 5, wherein the syringe barrel comprises a syringe tip, and wherein the hand-held syringe further comprises one of a catheter and a needle connected to the syringe tip to accept a fluid discharge from the syringe barrel as the plunger is advanced through the fluid receptacle.

13. The hand-held fluid delivery apparatus of claim 5, wherein a first movement of the first member relative to the second member via the hinge increases a spacing between the first and second gripping ends, increases a spacing between the plunger attachment end and the barrel attachment end, and moves the plunger relative to the syringe barrel along the longitudinal axis in a first direction, and wherein a second movement of the first member relative to the second member via the hinge decreases a spacing between the first and second gripping ends, decreases a spacing between the plunger attachment end and the barrel attachment end, and moves the plunger relative to the syringe barrel along the longitudinal axis in a second direction that is opposite of the first direction.

* * * * *